United States Patent [19]

Line et al.

[11] Patent Number: 4,734,364

[45] Date of Patent: * Mar. 29, 1988

[54] PRODUCTION OF DEXTROSE AND MALTOSE SYRUPS USING AN ENZYME DERIVED FROM RICE

[75] Inventors: William F. Line, Greenfield, Wis.; Vinod K. Chaudhary, Manhattan, Kans.; Etzer Chicoye, Milwaukee; Robert J. Mizerak, Waukesha, both of Wis.

[73] Assignee: Miller Brewing Company, Milwaukee, Wis.

[*] Notice: The portion of the term of this patent subsequent to Oct. 19, 1999 has been disclaimed.

[21] Appl. No.: 820,197

[22] Filed: Jan. 16, 1986

Related U.S. Application Data

[63] Continuation-in-part of Ser. No. 496,386, May 20, 1983, abandoned, and a continuation-in-part of Ser. No. 298,011, Aug. 31, 1981, abandoned, and a continuation-in-part of Ser. No. 263,156, May 13, 1981, Pat. No. 4,355,047, and a continuation-in-part of Ser. No. 263,154, May 13, 1981, Pat. No. 4,355,110, and a continuation-in-part of Ser. No. 141,536, Apr. 18, 1980, abandoned, and a continuation-in-part of Ser. No. 058,823, Jul. 19, 1979, abandoned.

[51] Int. Cl.$^4$ .................. C12P 19/22; C12P 19/16; C12P 19/20; C12N 9/44
[52] U.S. Cl. ........................... 435/95; 435/96; 435/98; 435/205; 435/209; 435/210; 435/814
[58] Field of Search .................. 435/95, 96, 98, 205, 435/209, 210, 814, 816

[56] References Cited

U.S. PATENT DOCUMENTS

| | | | |
|---|---|---|---|
| 2,891,869 | 6/1959 | Langlois | 99/142 |
| 3,137,639 | 6/1964 | Hurst et al. | 435/96 |
| 3,254,003 | 5/1966 | Croxall | 435/815 X |
| 3,565,765 | 2/1971 | Heady et al. | 195/31 |
| 3,716,455 | 2/1973 | Uedz et al. | 435/815 X |
| 3,897,305 | 7/1975 | Hurst | 195/31 R |
| 3,992,261 | 11/1976 | Takasaki et al. | 195/31 R |
| 3,996,107 | 12/1976 | Martensson | 195/31 R |
| 4,355,047 | 10/1982 | Line et al. | 435/210 X |

OTHER PUBLICATIONS

Dunn, G. and Manners, D., "The Limit Dextrinases from Ungerminated Oats and Ungerminated Rice", Carbohydrate Research, 39 pp. 283–293 (1975).

Primary Examiner—David M. Naff
Attorney, Agent, or Firm—Quarles & Brady

[57] ABSTRACT

A sugar syrup is prepared by saccharifying a liquefied starch hydrolyzate at a pH of about 4 to about 5.5 and a temperature above 55° C. with a heat stable, aciduric, pullulanase obtained from rice and an $\alpha$-1,4 carbohydrase. The pullulanase employed is substantially free of maltase and transglucosidase activity. In one embodiment, a dextrose syrup is prepared by saccharifying a thinned starch hydrolyzate with glucoamylase and the rice pullulanase. Maltose syrup is prepared using the rice pullulanase and a maltogenic enzyme.

4 Claims, No Drawings

PRODUCTION OF DEXTROSE AND MALTOSE SYRUPS USING AN ENZYME DERIVED FROM RICE

RELATED CASE

The present application is a continuation-in-part of our earlier application Ser. No. 058,823, filed July 19, 1979 now abandoned; Ser. No. 141,536, filed Apr. 18, 1980 now abandoned; Ser. No. 263,154, filed May 13, 1981 now U.S. Pat. No. 4,355,110; Ser. No. 263,156, filed May 13, 1981 now U.S. Pat. No. 4,355,047; Ser. No. 298,011 filed Aug 31, 1981 now abandoned and Ser. No. 496,386 filed May 20, 1983, now abandoned.

FIELD OF THE INVENTION

The present invention relates generally to a method of making starch-derived dextrose or maltose syrups. More particularly, it relates to a method of preparing dextrose or maltose syrups from starch under state of the art commercial production conditions using a heat-stable debranching enzyme extracted from rice.

DESCRIPTION OF THE PRIOR ART

At one time, the starch wet milling industry (hereafter "industry") produced all starch derived syrups by straight acid hydrolysis. There are several disadvantages of the acid process which are summarized in the Langlois U.S. Pat. No. 2,891,869. The problems noted therein were corrected when industry replaced the acid process with a two-step process calling for:

(1) solubilization or liquefaction of refined raw starch to low D.E. (dextrose equivalents i.e., reducing power relative to dextrose) syrups. This is accomplished by limited hydrolysis at high temperature using either acid or thermostable endoamylases such as those produced by *Bacillus lichenformis*.

(2) the low D.E. syrups produced in the first step are subjected to more extensive hydrolysis (or saccharification) to produce syrups consisting of low molecular weight sweet sugars using enzymes that are very specific with regard to the products they form.

The overall procedure is referred to as an acid-enzyme or double enzyme process depending on the mode of liquefaction.

U.S. Pat. No. 2,891,869, cited above, discloses the preparation of corn starch derived syrups using the acid-enzyme process. Syrups of varying composition were prepared depending upon the saccharifying enzymes employed. This patent teaches that fungal glucoamylase (GA) produces glucose as the sole product and that malt diastase produces the dissacharide maltose as the major end product. Syrups containing various proportions of these two sugars could be prepared by saccharifying the substrate with a combination of glucoamylase and malt diastase. Subsequent investigations have been concerned with the development of enzyme systems that increase the degree of starch saccharification and thereby the yields of these products.

High dextrose syrups have been important to industry for some time. These syrups have been used as sweetening adjuncts in the formulation of various foods and beverages and more recently as the substrate stream for the production of high fructose syrups. Industry produces high dextrose syrups by saccarification of liquefied starches with glucoamylase, as suggested by the Langelois' patent. Glucoamylases are dextrogenic exoamylases produced by various fungi (e.g., Aspergillus, Rhizopus). Most of the commercially available GA preparations are produced by Aspergillus sp. and are optimally active over the pH range 4.0–5.0 and are operationally stable at temperatures of 60° C. Industry is able to produce syrups containing about 90% dextrose by saccharifying acid or enzyme thinned low D.E. starches with GA at pH 4.3–4.5 at 60° C. for extended periods of time (e.g., 3–4 days).

Glucoamylases are capable of cleaving both the $\alpha$-1,4 and $\alpha$1,6 glycosidic bonds which occur in starch and in theory should be able to effect complete conversion. In practice, very high yields are obtained when the thinned starch is saccharified at a low solids level ($\leq 10\%$ w/w). However, when the saccharifications are conducted at solids levels demanded by industry (30–40% w/w), the dextrose content of the resultant syrup is substantially reduced due to the accumulation of higher DP saccharide impurities. However, industry had accepted syrups of lower dextrose content than desired due to the economic advantages gained by conducting the saccharification at a higher starch solids level.

Amylopectin is the principal component of industrially important starches. It is a mixed linkage glucose homopolymer in which the glucosyl moieties are linked by $\alpha$-1,4 and $\alpha$-1,6 glycosidic bonds. While glucoamylase is capable of hydrolyzing both, its activity vs $\alpha$-1,6 bonds or branchpoints is considerably less than vs $\alpha$-1,4 bonds. The diminished capacity vs the branchpoints impedes complete saccharification to dextrose using GA alone. The situation would be expected to improve if the branchpoints were more efficiently hydrolyzed.

In U.S. Pat. No. 3,897,305 by Thomas L. Hurst, a method is described for converting starch to dextrose by saccharifying a low D.E. starch stream with an enzyme system comprising glucoamylase and a starch debranching enzyme, amylo-1,6-glucosidase derived from *Aerobacter aerogenes* according to the method of Bender and Wallenfels (1). However, the process disclosed by Hurst suffers because it demands that the saccharification be conducted over temperature and pH ranges which are incompatible with the pH and temperature optima of glucoamylase itself. The preferred method called for saccharification of an enzyme liquified starch with GA and the amyloglucosidase over a pH range of 5.9–6.3 and temperatures of about 50° C. These conditions are far removed from the pH and temperature optima of 4.3 and 60° C., respectively, specified by various GA vendors. Using the Hurst conditions, the saccharifying power of the dextrogenic GA itself is dramatically reduced. This will be shown in Example 10 below.

Maltose syrups are desired by many foodstuffs' manufacturers because they are mildly sweet, do not crystallize at elevated solids, and are non-hygroscopic. Industry utilized maltogenic enzymes such as the malt diastase described by Langlois to produce maltose syrups containing 50–55% maltose. Unlike GA, most maltogenic enzymes (e.g., malt or sweet potato $\beta$-amylase) are completely devoid of debranching activity.

U.S. Pat. No. 3,565,765 discloses a method for increasing the maltose yield by using malt diastase in combination with the same amylo-1,6-glucosidase derived from *A. aerogenes* as disclosed by Hurst in U.S. Pat. No. 3,897,305 for the production of high dextrose syrups.

There are three basic classes of starch debranching enzymes. They are the glucoamylases, the isoamylases, and the pullulanases. The distinctions between these classes are well covered in a review article (Lee, E. and Whelan, J. "The Enzymes" 3rd Edition, V, 191, 1971). Basically, pullulanases cleave the α-1,6 linkages of pullulan (an α-1,6 polymer of maltotriose isolated from various molds) to yield maltotriose. Pullulanases, such as the amylo-1,6-glucosidase described by Bender and Wallenfels (1) and the one derived from rice as described below exhibit very little if any saccharifying power. Their utility in syrup production is as an adjunct to the main saccharifying enzyme, such as GA or malt diastase. They act by hydrolyzing the α-1,6 bonds in starch and permit the saccharifying enzyme to hydrolyze the resulting α-1,4 dextrins to syrups of the desired composition. In this way, starch is hydrolyzed to a greater degree and the yield and rate of formation of the desired products are increased.

Industry has several requirements of its saccharifying enzymes. As noted above, the enzymes must be capable of functioning at a high solids level. The enzymes must also be operationally stable at relatively high temperatures, i.e., they must be thermostable. The thermostability requirement is imposed for two reasons: (1) the risk of microbial contamination is reduced, and (2) the rate of saccharification is increased, which in turn enables industry to increase the production capacity of a given plant using existing equipment. Generally, industry requires that the saccharifying enzymes be thermostable at temperatures above 50° C. For example, they chose to use glucoamylase derived from Aspergillus over those produced by other genera, such as Rhizopus, solely because the former were more thermostable.

The bacterial debranching enzyme described in the Hurst patent lacks the thermostability required by industry. It is reported to be operationally stable up to 47.5° C. (2). This has meant that heretofore no saccharification in the presence of a debranching enzyme has been feasible much above this temperature whereas the dextrogenic and maltogenic enzymes GA and malt diastase are thermostable at 60° C.

In U.S. Pat. Nos. 4,355,047 and 4,355,110, we disclosed the extraction of a debranching enzyme from rice and its application in the preparation of low calorie beers when used as a fermentation adjunct together with a variety of α-1,4 carbohydrases including a variety of grain diastases and fungal glucoamylase. The debranching enzyme of these inventions was shown to be a pullulanase. We discovered that the rice enzyme had two unexpected properties which might make it useful in syrup production: (1) it was operationally stable to 60° C., and (2) it successfully debranched beer wort dextrins at the pH of fermenting beer which rapidly decreases from a high of 5.2 to ≦4.0 at high kraeusen. Thus, it appeared to satisfy the thermostability requirements of industry and to be aciduric enough to complement GA when used in dextrose syrup production. If so, it would represent a substantial improvement over the pullulanase derived from A. aerogenes described in the Hurst patent.

However, we discovered that the rice pullulanase preparation which we found to be effective in producing a super-attenuated low calorie beer could not be used in the preparation of starch derived syrups (e.g., dextrose and maltose syrups) because, in addition to pullulanase, it contained contaminating carbohydrase activities which adversely affect dextrose and maltose production.

The debranching enzymes described in our patents were obtained by extracting polished rice in buffers of moderate ionic strength. These extracts were later found to contain the following carbohydrases in addition to pullulanase: (1) both α- and β- amylase, and (2) a high level of maltase. The latter is obviously deleterious in the production of maltose syrups since it catalyzes the hydrolysis of maltose to glucose. Subsequently, it was shown that the same enzyme (i.e. maltase fraction) is undesirable in the production of dextrose syrups since it acts as a transglucosidase at high dextrose concentrations.

At the time our original application was filed, one other method of extracting the rice debrancher had appeared in the literature. Dunn and Manners (Carbohydrate Res. 39 283, 1979) prepared a rice limit dextrinase by extracting rice flour in 0.1 M acetate buffer. We have shown that extracts prepared according to Dunn and Manners contain about the same levels of maltase/-transglucosidase as the extract described in our original patent application and therefore could not be used to prepare the syrups described below.

Transglucosidases are enzymes that catalyze the formation of higher polymeric DP sugars from those of lower molecular weight. Transglucosidases are commonly encountered as trace contaminants of fungal glucoamylase preparations and commercial suppliers of these enzymes take great pains to remove them since their presence reduces the yield of the desired product (i.e., dextrose).

We have subsequently discovered methods of preparing a rice pullulanase which is substantially free of the maltase contaminant described above. The resulting rice pullulanase preparations are more thermostable than the pullulanase derived from A. aerogenes described in the Hurst patent and can be used to prepare high conversion maltose and dextrose syrups using the high saccharification temperatures demanded by industry. Furthermore, it is more aciduric than the bacterial pullulanase of Hurst and therefore can be used in the preparation of high conversion dextrose syrups over a pH range at which the dextrogenic enzyme glucoamylase is operating near peak efficiency. That is to say it is a better adjunct to GA in the preparation of dextrose syrups than the debranching enzyme disclosed by Hurst because it is similar to the dextrogenic enzyme in its pH and temperature properties.

SUMMARY OF THE INVENTION

It is the primary object of the present invention to disclose a method of preparing high dextrose syrups using a glucoamylase and a pullulanase derived from rice using the pH and temperature conditions commonly employed by industry.

Further objects of the invention are to disclose novel enzyme preparations containing a debranching enzyme extracted from ungerminated or germinated rice in which the enzyme is substantially freed of the contaminating maltase and transglucosidase referred to above, methods of preparing such novel enzyme preparations, and a method using the novel enzyme preparations in the production of high maltose syrups.

In the practice of the present invention, sugar syrups are prepared by adding a debranching enzyme or pullulanase from rice, which is substantially free of both maltase and transglucosidase activities, to either an acid or enzyme liquefied starch hydrolyzate in an effective amount to cleave the α-1,6 linkages of the starch so that an α-1,4 carbohydrase which is also present can convert the α-1,4 polysaccharides into the desired sugar syrup.

The debranching enzyme from rice has significant advantages over the pullulanases previously used in that it effectively debranches in a pH range of about 4.0 to about 5.3. Furthermore, it is surprisingly heat stable at about 55° C. to about 65° C. Thus it can be used to prepare dextrose at a pH near the optimum for glucoamylase and under commercial temperature conditions which results in higher DE syrups in shorter times compared to prior art pullulanase as illustrated in the Examples.

The invention also relates to a method of obtaining enzyme preparations from rice in which the debranching enzyme is free of maltase and transglucosidase activities and methods of removing the contaminant activities from preparations containing the debranching enzyme.

DESCRIPTION OF THE PREFERRED EMBODIMENT

The preferred enzyme preparations containing the rice debranching enzyme or pullulanase, which are substantially free of the maltase and transglucosidase contaminants, are prepared as described below.

When seed or polished rice is the starting material, a pullulanase preparation may be obtained, which is free of the maltase and transglucosidase contaminants, by extracting the rice in an aqueous buffer having an ionic strength <0.02 M buffer salts; preferably between zero and 0.008 M. When an extraction medium having an ionic strength much above 0.02 M buffer salts is used, increasing quantities of the maltase/transglucosidase are extracted.

In the preferred method, the rice is slurried in water at about 50° C. for about 3 hours. The enzyme solution is clarified by centrifugation, and the supernatant may be further purified by diafiltration and then concentrated to obtain an enzyme preparation containing the debranching enzyme free of the undesirable maltase and transglucosidase contaminants.

When malted rice is the starting material, the maltase/transglucosidase contaminants are coextracted with the pullulanase even when no buffer salts are added. Maltase/transglucosidase may be removed from pullulanase containing extracts by adsorbing one activity from another on weak ion exchangers. In the preferred method, the contaminating activities are selectively adsorbed on a weak cation exchange resin, e.g. carboxymethylcellulose or IRC-50 under conditions which reject pullulanase.

The debranching enzyme or pullulanase from rice, which has been extracted by the preferred method or otherwise substantially freed of the contaminating carbohydrases, is added to liquefied starch hydrolyzate together with a dextrogenic or maltogenic enzyme to form the desired sugar syrup. The effective amounts of the debranching and other enzyme to be added will depend upon the nature of the starch, the reaction conditions and the percentage of maltose or dextrose desired in the final syrup.

Normally, the rice enzyme will be present in an amount of at least about 0.001 units and preferably about 0.05 units to about 0.5 units of pullulanase activity per gram of dry substance (gds) of starch hydrolyzate and the α-1,4 carbohydrase will be present in an amount which is effective to convert the α-1,4 polysaccharides formed into the desired sugar syrup. Larger amounts of the debranching enzyme may be used but provide no particular advantage. On a unit to unit basis the rice pullulanase when added at identical levels is superior to the Hurst pullulanase under all conditions as illustrated in the Examples below.

The α-1,4 carbohydrase, which is most commonly used in the industry when a high dextrose syrup is desired, is a glucoamylase, such as that derived from *Aspergillus niger*, which will cleave α-1,4 linkages. The combination of the rice debranching enzyme and the glucoamylase significantly increases the yield and reduces the time normally required to prepare a high dextrose syrup with glucoamylase alone. Although both of the enzymes possess some α-1,6 debranching activity, the rice pullulanase is more potent than glucoamylase and as a result the reaction time is significantly reduced. The amount of the rice pullulanase in such a mixture will normally be at least 0.001 units and preferably will be from about 0.10 to about 0.5 units pullulanase/gds and the amount of glucoamylase will be at least about 0.01 units and preferably about 0.15 units to about 0.3 units of glucoamylase activity per gds. The reaction may be conducted at the same pH and temperature at which commercial preparations are normally made, i.e. a pH ranging from 4.0 to 5.3 and a temperature of about 55° C. to about 65° C.

The α-1,4 carbohydrase which is used when the desired product is a high maltose syrup is a maltogenic or maltose producing enzyme, such as sweet potato β-amylase. The amount of enzyme to be added is preferably the minimum amount required to convert the α-1,4 polysaccharides to maltose. Normally amounts of at least about 1 to about 4 units/gds are used. Larger amounts can be used but are less economical. The reaction is preferably conducted at a pH of about 4.5 to about 5.5 and a temperature of about 55° C. to 60° C.

The following analytical procedures were used in the examples described below:

Materials and Methods

A. Materials

Polished rice (#4 brewer's grade) was obtained from American Rice Institute, Houston, Tex. Maltrin M-100, a 10 D.E. acid thinned cornstarch, used as the substrate in these studies, was purchased from Grain Processing Corporation, Muscatine, Iowa. Pullulan was obtained from Enzyme Development Corporation, New York, N.Y. Linter starch was purchased from Rascher and Betzhold, Chicago, Ill. Maltose was obtained from Difco, Detroit, Mich. Glucoamylase AMG 150 (150 AMG units/ml) was purchased from NOVO Industries, Wilton, Connecticut. The pH optima of this enzyme was 4.3. The pullulanase derived from *A. aerogenes*, used in the Hurst and Heady patents was Enzeco K-2000 obtained from Enzyme Development Corp., New York, N.Y.

B. Methods

1. Enzyme Assay

Pullulanase and amylase activities were monitored by the appearance of reducing sugars using 3,5 dinitrosalycilic acid reagent [3]. The following substrates were used to identify the two activities: (1) pullulan for pullulanase activity and (2) Linter starch for amylase activity. In all cases the enzyme was incubated with the 0.5% w/v substrate at pH 5.0 and 50° C. A unit of activity in both assays is defined as the appearance of 1 mg reducing sugar (calculated as maltose) per minute under these conditions.

Rice maltase activity was determined by the hydrolysis of 0.5% w/v maltose at pH 5.0 and 50° C. The glucose released was monitored on the Model 27 Industrial Analyzer (Yellow Springs Instrument, Yellow Springs, Ohio). A unit of maltase activity is defined as the production of one mg glucose per minute under these conditions.

Glucoamylase activity was determined by the hydrolysis of 0.5% w/v maltose at 25° C. and pH 5.0. The glucose released was monitored by YSI glucose analyzer described above. A unit of activity is defined as the hydrolysis of 1 micromole maltose/minute under these conditions.

2. Carbohydrate Analyses

The carbohydrate composition of the syrups were determined by high pressure liquid chromatography (HPLC) using a HPX-87 prepacked column (7.8×300 mm, $Ca^{+2}$ form), which was obtained from Bio-Rad Laboratories, Richmond, Calif. The chromatograms were developed with $H_2O$ at a flow rate of 0.6 ml/min and a temperature of 85° C. on a Hewlett-Packard HP1084B apparatus equipped with a refractive index detector and a microprocessor controlled programmer/data module.

Prior to analyses, analytical samples of the hydrolysates were heated to 100° C. to inactivate the saccharifying enzymes and diluted to 6°–7° Brix to obtain a linear response. The results are presented as area percent.

3. Other

Protein was determined by the Miller modification of the Lowry method [4].

EXAMPLE 1

Extraction of Polished Rice Pullulanase in Various Media

Rice pullulanase was prepared by doughing 100 gm. floured polished rice into 200 ml of various extraction media. In each case the suspension was stirred for three hours at 50° C. The pullulanase containing extracts were clarified by straining through cheesecloth followed by centrifugation.

Table 1 lists the pullulanase and maltase activities of two preparations, one extracted in 0.1 M phosphate buffer and the second in tap water. Increasing the ionic strength of the media increased the extraction of the maltase contaminant whereas the pullulanase activity was fairly constant. Thus the maltase/pullulanase (M/P) ratio of preparation 1 was 30 times as high as that of preparation 2. Extracts containing unacceptably high maltase levels were obtained at buffer salts greater than 0.02M.

EXAMPLE 2

Extraction of Malted Rice and Removal of Maltase with Carboxymethyl Cellulose [CMC]

Seed grade LaBelle rice was steeped in water at 22° C. and then germinated for 5 days at the same temperature after which it was kilned at 50° C. Prior to extraction, the malted rice was floured and defatted with n-hexane.

The defatted flour was extracted under the same conditions as described for polished rice in preparation 2 in Example 1. The extract was dialyzed in 0.02M phosphate buffer pH 7.0 in preparation for treatment with CMC. The resin was added at the rate of 21 mg. (moist weight) per mg. protein and the resulting slurry was stirred for 1 hr. at room temperature. The maltase free, pullulanase supernatant was harvested by filtration.

The activity profiles of these preparations, 3 and 4, are given in Table 2. The $\beta$-amylase yield of the malted rice extract was increased about 20-fold over that obtained from ungerminated polished rice. However, the grain was sufficiently modified during germation so that the quantity of maltase extracted was unacceptably high even at low ionic strength. Treatment of the extract with CMC removed 77% of this contaminant and permitted the use of malted rice extracts in the preparation of high conversion maltose syrups.

EXAMPLE 3

Effect of Rice Maltase on Dextrose Yield

Polished rice preparations 1 and 2 (Table 1) were used together with fungal glucoamylase to prepare dextrose syrups at pH 5.0 and 55° C. The experimental syrups were compared to a glucoamylase control syrup saccharified at pH 4.3, the optimum for glucoamylase. The enzyme addition rates listed in Table 3 are given in units per gm dry substance (u/gds).

Table 3 lists the carbohydrate compositions of these syrups. The inclusion of both rice pullulanase preparations resulted in greater dextrin utilization. After 47 hours the dextrin level of both specials were about 28% of the control syrup. Despite this, the experimental syrup produced with the maltase containing preparation 1 contained less dextrose (DP-1) than the control. This was due to the production of DP-2 and DP-3 sugars, particularly the former. Thus, after 47 hours, the syrup contained 4.3 times as much DP-2 and 2.7 times as much DP-3 as the control. There was essentially no change after 96 hours.

When the maltase-free preparation 2 was used, the dextrose yield was increased 5% relative to the control and 9% relative to the syrup prepared with GA and preparation 1 after 47 hours. In contrast to the latter, this syrup contained about the same DP-2 and DP-3 levels as the control.

Equivalent syrups could be produced using preparation 1 if the maltase contaminant was removed by adsorption to CMC.

EXAMPLE 4 TO 10

Comparison of Rice Pullulanase and Aerobacter aerogenes Pullulanase in the Production of Dextrose syrups.

A series of experiments were conducted to compare the efficiencies of the polished rice pullulanase of preparation 2 (Table 1) and the bacterial pullulanase described by Hurst when both were used as adjuncts to glucoamylase in the preparation of dextrose syrups under a variety of conditions. In all cases, the GA addition rate was fixed at 0.15 u/gds while the two pullulanases were added at rates of 0.13 u/gds and 0.50 u/gds. The saccharification parameters investigated were pH, temperature, and solids level of the substrate. The experimental syrups were compared to controls prepared with glucoamylase alone under the same conditions except for pH. The controls were prepared at the pH of 4.3 where glucoamylase is optimally active and which is therefore the pH employed by industry.

The results of these studies are summarized in Table 4. In every case, the inclusion of rice pullulanase resulted in substantial increases in dextrose yield over GA

*alone operating at its optimum pH of 4.3.* The dextrose yields were increased from 2–4% depending on the pullulanase addition rate. This was true at temperatures of 55° C. (Examples 4 and 5) and 60° C. (Examples 6–8) and at saccharification pHs of 5.0 (Examples 4, 6, 8 and 9) and 4.5 (Examples 5 and 7). Even at 65° C., where glucoamylase is obviously inactivated, the rice pullulanase results in substantial increases in dextrose yield (Example 9). The rice pullulanase proved to be an effective adjunct to GA at both solids levels tested. Examination of the carbohydrate compositions listed in Table 4 reveal that rice pullulanase effected the increased dextrose yields at the expense of the dextrin fraction. Thus, the rice enzyme augmented the weak α-1,6 activity of GA and its inclusion resulted in more efficient debranching of the substrate. The increased debranching action resulted in more extensive hydrolysis of the substrate, lower dextrin levels, and increased dextrose yield in the experimental syrups.

In contrast, the bacterial pullulanase described by Hurst *failed* to increase the dextrose yield in virtually every case. The sole exception was in Example 4 (at 55° C. and pH 5.0 and then only when added at the higher addition rate (0.5 u/gds). However in this instance, it was even less effective than the rice pullulanase added at only 26% of the addition rate. In all other experiments, the experimental syrups prepared with the bacterial pullulanase and GA contained the same (Examples 4 and 5) or less (Examples 6, 7, 8, 9) dextrose than did GA alone operating at its optimum of 4.3. These experiments amply demonstrate that the use of rice pullulanase is a significant improvement over the use of the *A. aerogenes* enzyme described in the prior art because it is more aciduric and thermostable and therefore, it complements GA better in the production of dextrose syrups.

The data from Example 10 is interesting because these saccharification conditions (pH 6.0 and 55° C.) lie in the preferred range described by Hurst. In this case, there are two GA control syrups, one saccharified at pH 6.0 and the proper control prepared at pH 4.3. It is quite evident that GA is inefficient at the more alkaline pH. Thus, after 46 hours, the pH 6.0 control only contained 76% dextrose as opposed to about 92% for the 4.3 control syrup. Under these circumstances, one would expect that the syrups produced with either pullulanase and GA at pH 6.0 would be inferior to those produced with GA alone at pH 4.3 and this proved to be the case. However, here again rice pullulanase produced syrups containing 2% more dextrose than those produced with the bacterial pullulanase at identical addition rates.

Syrups containing about 96% dextrose were prepared by adding rice flour at the rate of 4.1% (based on starch solids) to a saccharification mixture containing the substrate at 30% w/w and GA 0.15 w/gds. The syrup was saccharified at pH 5.0 and 60° C.

EXAMPLE 11

Comparison of Pullulanases from Rice and Aerobacter aerogenes in the Production of Maltose Syrups.

Both rice pullulanase preparation 2 and the bacterial pullulanase from *A. aerogenes* were used as adjuncts to the maltogenic enzyme, sweet potato β-amylase, in the preparation of maltose syrups. The pH optimum of the β-amylase is reported to be 4.8 and it is operationally stable at 60° C., so these were the conditions used.

Table 5 summarizes the results of these studies. After 44 hours the control syrup contained about 56% maltose and the experimental syrup produced with β-amylase and rice pullulanase contained about 70% maltose. The dextrin fraction was reduced by 55% and 66% over that of the control syrup at 0.13 and 0.50 u/gds, respectively. In contrast, the bacterial pullulanase of Hurst produced syrups which contained 59–60% maltose during the same time frame. This enzyme only reduced the dextrin fraction 6% and 14% relative to the control at addition rates of 0.13 and 0.50 u/gds. The comparison demonstrates that rice pullulanase is more thermostable and aciduric than the bacterial enzyme described in the prior art. Further, it is optimally active over a rather broad pH range and may be employed as a saccharification adjunct with a wide variety of maltogenic enzymes at the high saccharification temperatures favored by industry.

Similar results may be obtained with the maltase containing polished rice preparation 1, providing the maltase contaminant is removed by adsorption to CMC.

EXAMPLE 12

Production of High Maltose Syrups with Malted Rice Extract.

Malted rice preparations 3 and 4 (Example 2, Table 2) were used to prepare high maltose syrups under conditions similar to those described for the polished rice pullulanase and the sweet potato β-amylase described above. These syrups were prepared at a pullulanase addition rate of 0.5 u/gds. The corresponding β-amylase and maltase addition rates are given in Table 6, which gives the carbohydrate distribution of these syrups. The maltase free preparation 4 yielded a syrup containing 67% maltose and 2.4% dextrose in 24 hours. The maltose concentration did not change much on further saccharification. In contast, the maltase containing preparation 3 yielded a syrup which contained less maltose and more dextrose. Prolonged hydrolysis increased dextrose at the expense of maltose. Thus, after 41 hours, the syrup prepared with preparation 3 contained 2.8% less maltose and 2.6% more dextrose than at 24 hours.

The foregoing examples demonstrate the utility of rice pullulanase as adjuncts to: (1) glucoamylase in the production of dextrose syrups, and (2) maltogenic enzymes, such as sweet potato β-amylase, in the production of maltose syrups. Rice pullulanase is an improvement over pullulanase produced by *A. aerogenes* described by Hurst because it is more thermostable and is optimally active at the high saccharification temperatures demanded by industry. When used in the production of dextrose syrups, rice pullulanase substantially increased the dextrose yield relative to control syrups produced with GA alone operating at its optimum pH. The bacterial pullulanase described by Hurst failed to increase the yield in every case. Similarly, when used to produce maltose syrups, the rice pullulanase operating with sweet potato β-amylase resulted in substantial increases in maltose yield. In contrast, the bacterial pullulanase of the prior art was not nearly as effective. The comparative tests contained in the examples clearly demonstrate that rice pullulanase is a substantial improvement over the bacterial pullulanase described in the prior art.

TABLE 1

Enzymatic Activity Profile of Rice Pullulanase Preparations

| Preparation Number | Extraction Buffer | Activity U/ml Pullulanase [P] | Maltase [M] | M/P |
|---|---|---|---|---|
| 1 | 0.1 M phosphate, pH 6.0 | 1.01 | 1.54 | 1.52 |
| 2 | Tap water | 1.04 | .05 | 0.05 |

TABLE 2

Enzymatic Activity Profile of Malted Rice

| Preparation Number | Extraction Buffer | CMC Treatment | Specific Activity Pullulanase [P] | Amylase [A] | Maltase [M] | M/P |
|---|---|---|---|---|---|---|
| 3 | water | — | 0.68 | 4.16 | 0.52 | 0.76 |
| 4 | water | + | 0.73 | 4.73 | 0.13 | 0.18 |

TABLE 3

Comparison of Rice Pullulanase Preparations 1 and 2 in the Preparation of Dextrose Syrups

| Saccharification pH | Temp °C. | Substrate % w/w | Pullulanase Preparation | Enzyme Rate U/gds Pullulanase | GA | Time (hrs) | DP-1 | DP-2 | DP-3 | Dextrin |
|---|---|---|---|---|---|---|---|---|---|---|
| 4.3 | 55 | 30 | — | — | 0.15 | 47 | 90.7 | 2.6 | 0.5 | 5.8 |
| 5.0 | 55 | 30 | 1 | 0.50 | 0.15 | 47 | 86.7 | 9.3 | 2.1 | 1.6 |
| 5.0 | 55 | 30 | 2 | 0.50 | 0.15 | 47 | 95.4 | 2.2 | 0.8 | 1.5 |
| 5.0 | 55 | 30 | 1 | 0.50 | 0.15 | 96 | 87.5 | 9.6 | 1.5 | 1.4 |

All sugars are identified by their degree of polymorization (DP number) e.g.
DP-1 = dextrose or glucose
DP-2 = maltose
DP-3 = trisaccharide predominantly maltotriose
Dextrin = all sugars greater than DP-3

TABLE 4

Comparison of Pullulanases From Rice and *Aerobacter Aerogenes* in the Production of Dextrose Syrups

| Example | Saccharification pH | Temp °C. | Substrate % w/w | Debrancher Source | Enzyme Rate U/gds Debrancher | GA | Time (hrs) | DP-1 | DP-2 | DP-3 | Dextrin |
|---|---|---|---|---|---|---|---|---|---|---|---|
| 4 | 4.3 | 55 | 30 | — | — | 0.15 | 46 | 91.39 | 1.64 | 0.56 | 6.51 |
| 4 | 5.0 | 55 | 30 | bacterial | 0.13 | 0.15 | 46 | 91.85 | 1.65 | 0.50 | 6.00 |
| 4 | 5.0 | 55 | 30 | bacterial | 0.50 | 0.15 | 46 | 93.73 | 1.79 | 0.81 | 3.67 |
| 4 | 5.0 | 55 | 30 | rice | 0.13 | 0.15 | 46 | 94.39 | 1.96 | 0.81 | 2.84 |
| 4 | 5.0 | 55 | 30 | rice | 0.50 | 0.15 | 46 | 95.12 | 2.34 | 0.91 | 1.62 |
| 5 | 4.3 | 55 | 30 | — | — | 0.15 | 48 | 92.60 | 1.80 | 0.44 | 5.38 |
| 5 | 4.5 | 55 | 30 | bacterial | 0.13 | 0.15 | 48 | 92.46 | 1.82 | 0.46 | 5.26 |
| 5 | 4.5 | 55 | 30 | bacterial | 0.50 | 0.15 | 48 | 92.51 | 1.79 | 0.45 | 5.25 |
| 5 | 4.5 | 55 | 30 | rice | 0.13 | 0.15 | 48 | 94.54 | 1.83 | 0.61 | 3.01 |
| 5 | 4.5 | 55 | 30 | rice | 0.50 | 0.15 | 48 | 95.59 | 2.11 | 0.70 | 1.60 |
| 6 | 4.3 | 60 | 30 | — | — | 0.15 | 48 | 92.15 | 1.92 | 0.56 | 5.37 |
| 6 | 5.0 | 60 | 30 | bacterial | 0.13 | 0.15 | 48 | 90.31 | 1.42 | 0.40 | 7.87 |
| 6 | 5.0 | 60 | 30 | bacterial | 0.50 | 0.15 | 48 | 90.73 | 1.69 | 0.43 | 7.15 |
| 6 | 5.0 | 60 | 30 | rice | 0.13 | 0.15 | 48 | 94.22 | 1.91 | 0.67 | 3.20 |
| 6 | 5.0 | 60 | 30 | rice | 0.50 | 0.15 | 48 | 95.02 | 1.69 | 0.43 | 1.94 |
| 7 | 4.3 | 60 | 30 | — | — | 0.15 | 46 | 91.62 | 1.55 | 0.43 | 6.39 |
| 7 | 4.5 | 60 | 30 | bacterial | 0.13 | 0.15 | 0.46 | 91.38 | 1.75 | 0.60 | 6.27 |
| 7 | 4.5 | 60 | 30 | bacterial | 0.50 | 0.15 | 46 | 91.04 | 1.84 | 0.64 | 6.48 |
| 7 | 4.5 | 60 | 30 | rice | 0.13 | 0.15 | 46 | 93.15 | 2.35 | 0.70 | 3.82 |
| 7 | 4.5 | 60 | 30 | rice | 0.13 | 0.15 | 46 | 94.68 | 2.01 | 0.76 | 2.55 |
| 8 | 4.3 | 60 | 40 | — | — | 0.15 | 93 | 91.76 | 3.92 | 0.70 | 3.63 |
| 8 | 5.0 | 60 | 40 | bacterial | 0.13 | 0.15 | 93 | 90.57 | 3.24 | 0.61 | 5.58 |
| 8 | 5.0 | 60 | 40 | bacterial | 0.50 | 0.15 | 93 | 90.70 | 3.79 | 0.85 | 4.69 |
| 8 | 5.0 | 60 | 40 | rice | 0.13 | 0.15 | 93 | 93.48 | 3.30 | 0.83 | 2.38 |
| 8 | 5.0 | 60 | 40 | rice | 0.50 | 0.15 | 93 | 94.05 | 3.77 | 0.87 | 1.31 |
| 9 | 4.3 | 65 | 40 | — | — | 0.15 | 45 | 87.61 | 3.33 | 0.62 | 8.43 |
| 9 | 5.0 | 65 | 4.0 | bacterial | 0.13 | 0.15 | 45 | 82.49 | 3.21 | 0.91 | 13.40 |
| 9 | 5.0 | 65 | 40 | bacterial | 0.50 | 0.15 | 45 | 82.80 | 3.04 | 0.74 | 13.43 |
| 9 | 5.0 | 65 | 40 | rice | 0.13 | 0.15 | 45 | 89.03 | 3.61 | 1.07 | 6.29 |
| 9 | 5.0 | 65 | 40 | rice | 0.50 | 0.15 | 45 | 91.31 | 4.18 | 1.20 | 3.31 |
| 10 | 6.0 | 55 | 30 | — | — | 0.15 | 46 | 75.85 | 3.25 | 0.36 | 20.53 |
| 10 | 4.3 | 55 | 30 | — | — | 0.15 | 46 | 91.39 | 2.14 | 0.45 | 6.02 |
| 10 | 6.0 | 55 | 30 | bacterial | 0.13 | 0.15 | 46 | 82.90 | 3.28 | 0.57 | 13.25 |
| 10 | 6.0 | 55 | 30 | bacterial | 0.50 | 0.15 | 46 | 85.50 | 4.44 | 0.59 | 9.12 |
| 10 | 6.0 | 55 | 30 | rice | 0.13 | 0.15 | 46 | 84.67 | 4.54 | 0.69 | 10.10 |
| 10 | 6.0 | 55 | 30 | rice | 0.50 | 0.15 | 46 | 87.64 | 6.45 | 0.87 | 5.04 |

TABLE 5

Comparison of Pullanases From Rice and *Aerobactor Aerogenes* in the Production of Maltose Syrups

| Example | Saccharification pH | Temp °C. | Substrate % w/w | Debrancher Source | Enzyme Rate U/gds Debrancher | β-amylase | Time (hrs) | DP-1 | DP-2 | DP-3 | Dextrin |
|---|---|---|---|---|---|---|---|---|---|---|---|
| 11 | 4.8 | 60 | 30 | — | — | 3.6 | 44 | 1.58 | 56.28 | 10.68 | 31.47 |
| 11 | 4.8 | 60 | 30 | bacterial | 0.13 | 3.6 | 44 | 1.30 | 58.02 | 11.18 | 29.51 |
| 11 | 4.8 | 60 | 30 | bacterial | 0.50 | 3.6 | 44 | 1.58 | 59.87 | 11.60 | 29.94 |
| 11 | 4.8 | 60 | 30 | rice | 0.13 | 3.6 | 44 | 2.04 | 69.52 | 14.37 | 14.07 |
| 11 | 4.8 | 60 | 30 | rice | 0.50 | 3.6 | 44 | 4.52 | 69.55 | 15.35 | 10.58 |

TABLE 6

Preparation of Maltose Syrups with Malted Rice Extracts

| Malted Rice Preparation | Enzyme Addition U/gds | | | Time (hrs) | Carbohydrate % | | | |
|---|---|---|---|---|---|---|---|---|
| | Pullulanase | β-Amylase | Maltase | | DP-1 | DP-2 | DP-3 | Dextrin |
| 3 | 0.5 | 3.06 | 0.38 | 24 | 7.1 | 58.2 | 20.3 | 14.4 |
| 3 | 0.5 | 3.06 | 0.38 | 41 | 9.7 | 55.4 | 22.9 | 12.0 |
| 4 | 0.5 | 3.24 | 0.09 | 24 | 2.4 | 67.0 | 17.7 | 12.9 |
| 4 | 0.5 | 3.24 | 0.09 | 41 | 3.5 | 67.4 | 18.7 | 10.4 |

The rice which may be used as the source of the enzyme of the present invention is food-grade rice which has been treated at conditions mild enough to preserve the enzymatic activity. If ungerminated rice is used, either seed or polished dry milled rice may be used. However, the preferred source is commercially polished dry milled brewer's rice because ease of procurement, higher specific activity yield and economy. The enzyme may be extracted from a wide variety of seed grade rice including LaBelle, LeBonnet, Nato, Starbonnet, or Brazos. LaBelle was chosen for the examples since it is the most plentiful domestic variety.

It also will be apparent to those skilled in the art that a number of modifications and changes can be made without departing from the spirit and scope of the present invention. Therefore, it is intended that the scope of the invention be limited only by the claims which follow.

REFERENCES

1. Bender and Wallenfels, Methods in Enzymology, Vol. VIII, pg. 555–559, 1966.
2. Bender and Wallenfels Biochemische Feit; 334 79, 1961.
3. Bernfield, P. Advances in Enzymology XII (Nord, F, ed.) pg. 379, Interscience Publishers, New York, 1951.
4. Miller, G. Anal. Chem. 31, 964, 1969.

We claim:

1. In the method of preparing a sugar syrup from starch which comprises saccharifying a liquified starch hydrolyzate with an enzyme system which includes an α-1,6 debranching enzyme and an α-1,4 carbohydrase at a pH of about 4 to about 5.5, and a temperature of above 55° C. to about 65° C., the improvement which comprises employing as the α-1,6 debranching enzyme a heat-stable, pullulanase derived from rice, said pullulanase being essentially free of interfering maltase and transglucosidase activity.

2. The method of claim 1 in which the α-1,4 carbohydrase is glucoamylase and the syrup is a dextrose syrup.

3. The method of claim 1 in which the α-1,4 carbohydrase is a maltose producing enzyme and the syrup is a maltose syrup.

4. The method of claim 1, in which both the pullulanase and the α-1,4 carbohydrase are derived from malted rice and the syrup is a maltose syrup.

* * * * *